US010933382B2

United States Patent
Cai et al.

(10) Patent No.: US 10,933,382 B2
(45) Date of Patent: Mar. 2, 2021

(54) SUPPORTED ZEOLITE MEMBRANES

(71) Applicant: NOVOREACH Technologies LLC, Midland, MI (US)

(72) Inventors: Jun Jason Cai, Midland, MI (US); Jia Julia Liu, Midland, MI (US)

(73) Assignee: Novoreach Technologies LLC, Midland, MI (US)

( * ) Notice: Subject to any disclaimer, the term of this patent is extended or adjusted under 35 U.S.C. 154(b) by 0 days.

(21) Appl. No.: 16/631,073

(22) PCT Filed: Jul. 17, 2018

(86) PCT No.: PCT/US2018/000122
§ 371 (c)(1),
(2) Date: Jan. 14, 2020

(87) PCT Pub. No.: WO2019/017999
PCT Pub. Date: Jan. 24, 2019

(65) Prior Publication Data
US 2020/0147560 A1    May 14, 2020

Related U.S. Application Data

(60) Provisional application No. 62/604,723, filed on Jul. 18, 2017.

(51) Int. Cl.
*B01D 71/02* (2006.01)
*B01D 61/36* (2006.01)
(Continued)

(52) U.S. Cl.
CPC ........... *B01D 71/028* (2013.01); *B01D 61/36* (2013.01); *B01D 67/0051* (2013.01);
(Continued)

(58) Field of Classification Search
CPC .. B01D 71/028; B01D 61/36; B01D 67/0051; B01D 69/02; B01D 69/12; C07C 29/76
(Continued)

(56) References Cited

U.S. PATENT DOCUMENTS 5,296,344 A    3/1994    Jimbo et al.

OTHER PUBLICATIONS

Yan et al. The hydrothermal transformation of solid geopolymers into zeolites, Microporous and Mesoporous Materials. 161, 2012, p. 187-192.*

(Continued)

*Primary Examiner* — Deborah D Carr
(74) *Attorney, Agent, or Firm* — Karen L. Kimble; Tim S. Stevens; Technology Law PLLC

(57) ABSTRACT

An asymmetric membrane having a layer containing a zeolite supported on a geopolymer substrate and methods for making an asymmetric membrane having a layer containing a zeolite supported on a geopolymer substrate. A cross-flow membrane separation method for increasing the concentration of ethanol from a feed mixture comprising water and ethanol, comprising: cross-flowing a feed mixture comprising water and ethanol across the layer comprising a zeolite of the asymmetric membrane of the instant invention to produce a permeate having an ethanol concentration less than the ethanol concentration of the feed mixture and a retentate having an ethanol concentration greater than the ethanol concentration of the feed mixture, the pressure of the feed mixture being greater than the pressure of the permeate.

25 Claims, 1 Drawing Sheet

(51) Int. Cl.
  *B01D 67/00* (2006.01)
  *B01D 69/02* (2006.01)
  *B01D 69/12* (2006.01)
  *C07C 29/76* (2006.01)
(52) U.S. Cl.
  CPC .......... *B01D 69/02* (2013.01); *B01D 69/12* (2013.01); *C07C 29/76* (2013.01); *B01D 2315/10* (2013.01); *B01D 2325/022* (2013.01)
(58) Field of Classification Search
  USPC ........................................................ 560/920
  See application file for complete search history.

(56) References Cited

OTHER PUBLICATIONS

Azarhab et al. Ceramic membrane synthesis based on alkali activated blast funace slag for separation of water from ethanol, 42, 2016, p. 15568-15574.*

Yan He, Xue-min Cui, Xing-dong Liu, Yi-pin Wang, Jin Zhang, Kun Liu, "Preparation of self-supporting NaA zeolite membranes using geopolymers", J. of Membrane Sci., 447 (2013) 66-72.

He Yan, Cui Xue-min ⇑, Mao jin, Liu Le-ping, Liu Xing-dong, Chen Jin-yu, "The hydrothermal transformation of solid geopolymers into zeolites", Microporous and Mesoporous Materials, 161 (2012), 187-192.

Jin Zhang, YanHe, Yi-pinWang, JinMao, Xue-minCui, "Synthesis of a self-supporting faujasite zeolite membrane using geopolymergelforseparationofalcohol/watermixture", Materials Letters, 116 (2014) 167-170.

Mohammadreza Azarshab, Farzaneh Mohammadi, Hojjatollah Maghsoodloorad, Toraj Mohammadi, "Ceramic membrane synthesis based on alkali activated blast furnace slag for separation of water from ethanol", Ceramics International, 42 (2016) 15568-15574.

N.K. Lee a, Hammad R. Khalid b, H.K. Lee, "Synthesis of mesoporous geopolymers containing zeolite phases by a hydrothermal treatment", Microporous and Mesoporous Materials 229 (2016) 22e30.

* cited by examiner

SUPPORTED ZEOLITE MEMBRANES

BACKGROUND OF THE INVENTION

The instant invention relates to separation based technology and more specifically to membrane separation technology. Membrane separation can be an energy and capital efficient process providing low operating cost compared with other separation processes such as distillation. Polymeric membranes have been widely used but polymeric membranes fall short of performance requirements in some separation applications due to the limitations of their polymeric nature. For example, polymeric membranes generally operate a relatively low temperatures and can suffer performance degradation in the presence of organic compounds that exist in many industrial processes. In addition, the separation selectivity and permeation flux of polymeric membranes are relatively low for many separation applications. Compared with polymeric membranes, inorganic membranes, including zeolites, have distinct advantages because of their high chemical resistance, high thermal stability, high separation selectivity and high permeation flux. Since zeolites have uniform pore size, a specific constituent can be separated from a mixture by the difference in molecular size using a zeolite membrane. Zeolite membranes can be used in many separation applications in chemical, petrochemical, gas and energy, environmental, biological, food and drink, and other industries. Specific examples include dehydration of organic solvents, separation of oil and water mixtures, wastewater treatment, purification of wines and juices, purification and separation of gases, and other applications.

Fabrication of practical zeolite membranes is critical to large scale industrial application of zeolite membranes. Zeolite membranes are brittle and have poor mechanical strength that severely limits the fabrication and use. To overcome this problem, porous substrates are used to provide mechanical strength to zeolite membranes. A variety of substrate materials have been used to fabricate supported zeolite membranes in the prior art, including ceramics such as alumina, mullite, silica, titania, and zirconia, as well as metals such as stainless steel, nickel, and aluminum. Despite the advances in the art there remains a need for lower cost aluminum. Despite the advances in the art there remains a need for lower cost supported zeolite membranes and improved lower cost methods for making supported zeolite membranes.

SUMMARY OF THE INVENTION

In one embodiment, the instant invention is an asymmetric membrane, comprising: a layer comprising a zeolite supported on a geopolymer substrate. In another embodiment, the instant invention is a method for making an asymmetric membrane, comprising: (a) preparing a geopolymer composition; (b) forming a geopolymer substrate with the geopolymer composition; (c) depositing zeolite seed crystals on the geopolymer substrate to form a seeded geopolymer substrate; (d) coating the seeded geopolymer substrate with a composition comprising silica and alumina source materials to form a coated geopolymer substrate; (e) subjecting the coated geopolymer substrate to hydrothermal synthesis to form a layer comprising a zeolite on the geopolymer substrate. In yet another embodiment the instant invention is a method for making an asymmetric membrane, comprising: (a) preparing a geopolymer composition; (b) forming a geopolymer substrate with the geopolymer composition under conditions that produce zeolite crystals in the geopolymer substrate; (c) coating the geopolymer substrate with a composition comprising silica and alumina source materials to form a coated geopolymer substrate; (e) subjecting the coated geopolymer substrate to hydrothermal synthesis to form a layer comprising a zeolite on the geopolymer substrate. In another embodiment, the instant invention is a cross-flow membrane separation method for increasing the concentration of ethanol from a feed mixture comprising water and ethanol, comprising: cross-flowing a feed mixture comprising water and ethanol across the layer comprising a zeolite of the asymmetric membrane of the instant invention to produce a permeate having an ethanol concentration less than the ethanol concentration of the feed mixture and a retentate having an ethanol concentration greater than the ethanol concentration of the feed mixture, the pressure of the feed mixture being greater than the pressure of the permeate. The asymmetric membranes of the instant invention increase the effective permeable area of the zeolite containing layer. The asymmetric membranes of the instant invention can be arranged in more flexible design configurations.

DETAILED DESCRIPTION OF THE INVENTION

Figure 1:
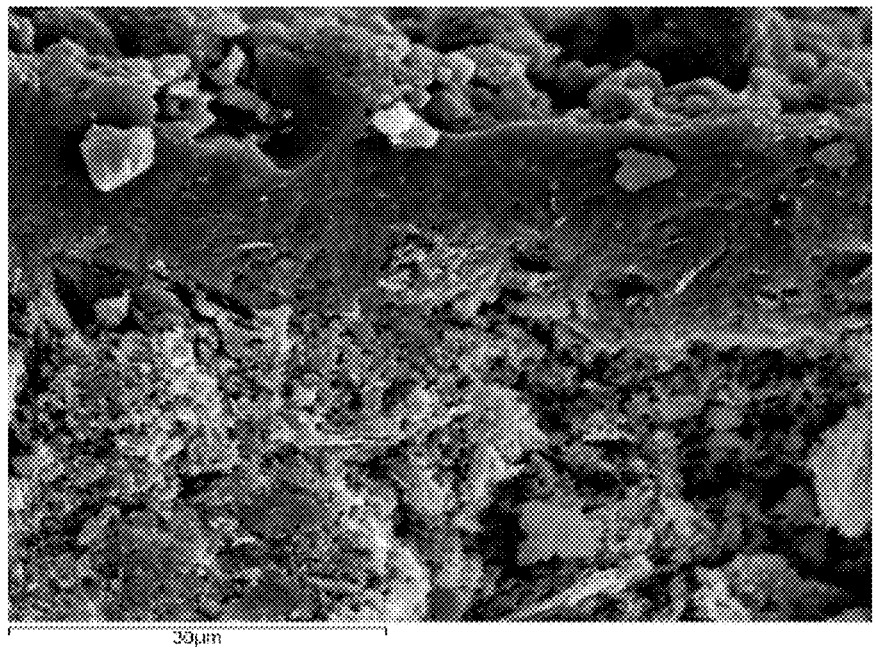
FIG. 1 is a scanning electron microscopic cross-sectional view of the asymmetric membrane of Example 2 wherein an upper layer comprising a zeolite is shown on a geopolymer substrate.
Figure 2:
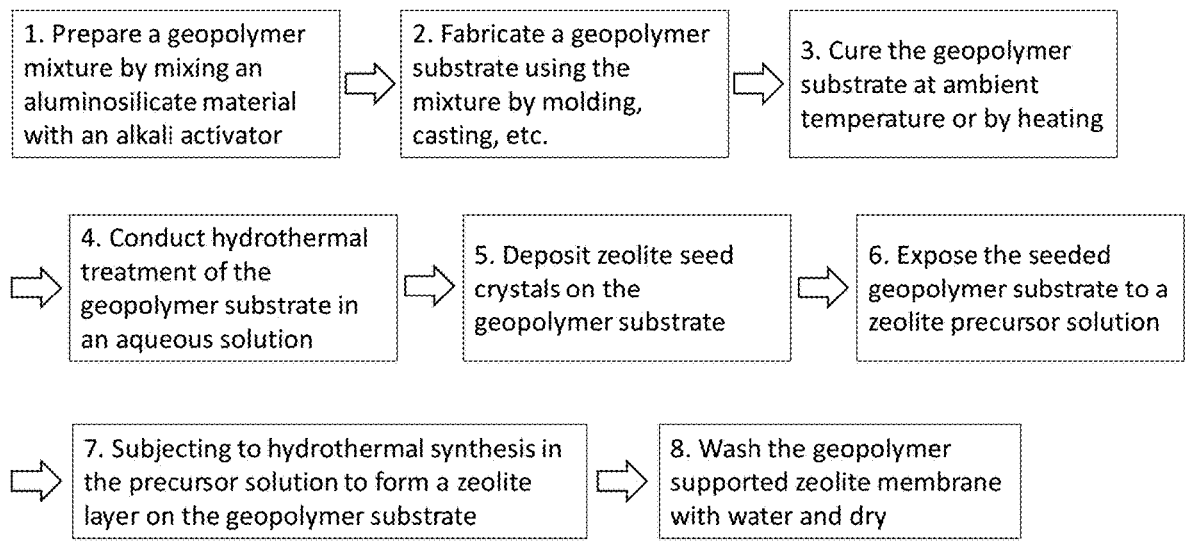
FIG. 2 depicts method steps for forming an asymmetric membrane of the instant invention.

Supported zeolite membranes are normally fabricated by placing a supporting substrate in a zeolite synthesis precursor solution followed by hydrothermal treatment under optimal conditions of temperature, pressure, and time. The zeolite membrane synthesis can, for example, be a one-step growth or a two-step growth process (secondary growth process). In the one-step process, zeolite crystals are grown directly on the substrates. In the two-step process, preformed zeolite crystal seeds are first coated on the substrates and zeolite hydrothermal synthesis is carried out. Coating of the substrates with zeolite seeds prior to zeolite hydrothermal synthesis is the prevailing practice in the art to facilitate formation of zeolite membranes by enhancing the crystallization of zeolites on the substrate surface rather than in the bulk of the zeolite synthesis precursor solution. After zeolite membranes are formed on a substrate, the supported zeolite membrane is normally washed with water and dried for separation applications.

While the use of conventional porous ceramic or metallic substrates provides structural robustness required for the fabrication and subsequent use of zeolite membranes, it also creates a number of problems, limiting the use of supported zeolite membranes. First, as the fabrication of porous ceramic or metallic substrates requires high quality raw materials, careful porous microstructure design, and high temperature processing, they are expensive and account for the majority of the overall zeolite membrane cost. This leads to high cost of supported zeolite membranes and limits their use in industrial separation applications. Second, since common ceramic or metallic substrate materials are non-conductive to permeating species, the solid and nonporous part of the substrates block the pores of a major part of the zeolite membrane at the substrate-membrane interface. This results in a significant reduction of the membrane area through which permeating species can flow out from the interface and hence the effective permeating area of supported zeolite membranes is only a fraction of the total exposed surface area of the zeolite membranes. Third, due to conventional ceramic or metal fabrication and high temperature processing requirements, porous ceramic or metallic substrates are usually fabricated with standard planar or tubular geometries and sizes, limiting separation membrane and module design flexibility. To reduce membrane fabrication cost, improve membrane separation performance, and increase membrane design flexibility, the present invention discloses a supported zeolite membrane manufacturing process and supported zeolite membrane based on a geopolymer as the substrate material.

Geopolymers are a type of crosslinked long-chain aluminum silicate inorganic polymeric material between tetrahedral $AlO_4$ and $SiO_4$ units with build-in three-dimensional structure and excellent material properties such as high strength and thermal and chemical stability. The general formula of geopolymers is $M_n[-(SiO2)_z-(AlO2)-]_n$, where M is a monovalent cation, z is the ratio of Si to Al, and n is the degree of polymerization. M is typically an alkali metal such as lithium, sodium, potassium, or other monovalent cations. The formation of a geopolymer usually involves an aluminosilicate source such as calcined clay or fly ash and an alkali activator solution generally comprising alkali hydroxide and alkali silicate. One unique characteristic of geopolymer materials is their ability to polymerize and develop high strength at ambient or slightly elevated temperatures. As geopolymers are made of in-expensive raw materials and cured at near ambient temperatures, geopolymer substrates have much lower fabrication cost compared with conventional ceramic or metallic substrates used for zeolite membrane fabrication. Furthermore, the ability of geopolymers to form solid ceramic-like materials at near ambient temperatures allows the use of not only ceramic membrane processing techniques but also polymeric membrane fabrication techniques, increasing membrane design flexibility and reducing processing cost.

Since geopolymers are an aluminum silicate inorganic polymeric material, depending on the composition, cured geopolymer can be partly converted in the instant invention to zeolite by hydrothermal treatment in water or other media or simply heating in the presence of the moisture. The type of zeolite formed after the treatment depends on the geopolymer composition and hydrothermal treatment conditions. In addition, the mechanical strength of geopolymer are generally improved by the post-curing hydrothermal treatment. Thus the post-curing hydrothermal treatment of geopolymers results in the formation of high strength geopolymer-zeolite composite with zeolite crystals incorporated in the geopolymer microstructure. Since zeolites have uniform sized pores within their microstructure, permeating species can be transported in those pores as long as the pore size is larger than the size of the permeating species. The formation of zeolite crystals in the geopolymer microstructure leads to the increase in effective permeating area and higher substrate permeability compared with conventional ceramic or metallic substrates with similar porous microstructure.

Geopolymers have been used in the past to fabricate membranes for a number of separation applications such as dehydration of organic solvents and water purification. Some membranes are fabricated directly using geopolymer and others are fabricated using geopolymer followed by hydrothermal treatment in water or other media. However, it is not practically feasible to fabricate defect free geopolymer or geopolymer-zeolite composite membranes with high selectivity and permeation flux for separation applications. Geopolymer membranes have low separation selectivity due to the presence of defects in geopolymer membranes originated from the geopolymer mixture preparation and curing process. Increasing geopolymer membrane thickness to more than a few millimeter or centimeters has the potential to improve separation selectivity but at the same time significantly reduce permeation flux to a degree that is not practical for separation applications.

To achieve membrane separation with high permeation flux, an asymmetric member structure can be used in the instant invention to form a thin functional zeolitic separation layer formed on top of a porous geopolymer substrate. In the present invention, a method of manufacturing supported zeolite membranes with an asymmetric membrane structure is disclosed to use geopolymer to fabricate membrane substrates followed by forming zeolite membrane on geopolymer substrate surface. The geopolymer substrates are fabricated by mixing an aluminum silicate material with an alkali activator and curing at ambient or slightly elevated temperatures. The cured geopolymer substrates can be further hydrothermally treated in water or other media to in-situ convert part of the geopolymer to zeolite and form geopolymer-zeolite composite substrates with high permeation flux.

The zeolite membranes can be formed on the geopolymer substrates using any known method disclosed in prior art. For example, the secondary growth method can be used by seeding the geopolymer substrates before zeolite membrane synthesis. The zeolite seed application can be performed by various coating processes, including rubbing, brushing, dip-coating, vacuum application, flow-coating, and others known to those skilled in the field. The geopolymer substrates can be seeded with zeolite seed crystals at different geopolymerization stages, including before geopolymer curing, after geopolymer curing and before geopolymer hydrothermal treatment, and after geopolymer hydrothermal treatment and before zeolite hydrothermal synthesis. Compared with conventional ceramic or metallic substrates that require high temperature processing and only permit seeding after substrate are fabricated, geopolymer substrates allow seeding at any stage in the substrate fabrication process due to the low temperature geopolymer curing process, enabling good adhesion of zeolite seeds to substrate surface and reducing the possibility of zeolite seed falling off after seeding. The seeded geopolymer substrates are then subjected to zeolite membrane hydrothermal synthesis in a zeolite synthesis precursor solution with a composition suitable to produce desired zeolites, under appropriate processing conditions including temperature, pressure, and time, to form zeolite membranes on geopolymer substrates. The geopolymer supported zeolite membranes are washed, dried, or optionally heat treated at high temperatures to remove any zeolite synthesis templates used before their use in separation applications.

The use of geopolymer to fabricate geopolymer substrates for the manufacturing of supported zeolite membranes offers a number of advantages over conventional supported zeolite membrane manufacturing process: eliminating the need to use expensive high temperature processed porous ceramic or metallic substrates, enabling low temperature fabrication of membrane substrates with a variety of shapes and geometries, and improving permeation flux by increasing the effective permeating area of the supported zeolite membranes through in-situ formation of zeolite crystals in the geopolymer substrates by post-curing hydrothermal treatment. Furthermore, in the present invention, the geopolymer substrates do not require the use of masking material, tape, or sealing parts to prevent the contact of zeolite synthesis precursor solutions with the un-seeded side of the substrates in the zeolite membrane hydrothermal synthesis process, which is required in the prior art in the manufacturing of zeolite membranes supported on conventional ceramic or metallic substrates to prevent the blockage of substrate pores and as a result a reduction in membrane permeation flux.

The following are details useful in the instant invention:

(a) Geopolymer composition: Geopolymer materials can be synthesized by mixing an aluminosilicate source material, an alkali activator material, and a carrier fluid. The carrier fluid can part of the alkali activator material or aluminosilicate source material. The general formula of geopolymers is $M_n[-(SiO2)_z-(AlO2)-]_n$, where M is a monovalent cation, z is the ratio of Si to Al, and n is the degree of polymerization. M is typically an alkali metal such as lithium, sodium, potassium, or other monovalent cations and z is typically 1, 2, 3, or higher up to 32. The geopolymer substrates can be fabricated using any suitable composition defined by the general formula of geopolymer.

(b) An aluminosilicate source: The geopolymer composition according to the invention generally includes an aluminosilicate source. Any aluminosilicate materials known in the art, or combinations thereof, may be used. Exemplary aluminosilicate materials include, but are not limited to metakaolin, calcined kaolin clays, fly ash, blast furnace slags, phosphate type clays, aluminum-containing silica fume, natural aluminosilicate, aluminosilicate glass powder, vitreous calcium aluminosilicate, zeolite, scoria, allophone, bentonite, pumice, and others. A significant part of these aluminosilicate materials is amorphous aluminosilicate phase which reacts easily with strong alkali solutions. It is preferred that the aluminosilicate source is metakaolin, calcined clays, fly ash, slags, or a combination of two or more of these materials.

(c) An alkali activator: The geopolymer composition according to the invention generally includes an alkali activator. The alkali activator generally comprises an alkali metal or alkaline earth metal silicate component and an alkali metal or alkaline earth metal hydroxide component. References herein to "alkali" compounds are intended to refer to alkali metals (e.g., Li, Na, and K) and alkaline earth metal (e.g., Mg, Ca) compounds. The alkali silicate component comprises at least one of sodium silicate, potassium silicate, lithium silicate, calcium silicate or magnesium silicate. The alkali silicate component preferably comprises sodium silicate. The alkali hydroxide component comprises at least one of sodium hydroxide, potassium hydroxide, lithium hydroxide and the like, preferably sodium hydroxide.

(d) A carrier fluid: The geopolymer composition according to the invention generally includes a carrier fluid. The carrier fluid can be water, organic solvents, other liquids, or a combination of two or more fluids. It is preferred that the carrier fluid is water. If the aluminosilicate source or metal hydroxide activator is already in a liquid state, it is considered that the geopolymer composition already has a carrier fluid within.

(e) Geopolymer substrate fabrication: After geopolymer mixtures are prepared, they can be fabricated into any shape and geometry without particular limitation, and may be in a form of, for example, plate, tube, sphere, monolith, or honeycomb using conventional ceramic or organic polymer processing methods including molding, slip casting, tape casting, centrifugal casting, spin casting, extrusion, etc.

(f) Geopolymer substrate curing temperature and time: The curing of the geopolymer mixture can be conducted at ambient temperature or by raising the temperature of the geopolymer mixture by providing a heat source. The heating can be achieved by convection, radiation, or conduction methods. The curing can be carried out at a temperature between 20 and 200° C., preferably between 30 and 150° C., more preferably between 40 and 120° C., and even more preferably between 50 and 90° C. The curing of the geopolymer composition may be conducted generally between 1 and 168 h, preferably between 1 and 72 hours, more preferably between 4 to 48 hours, even more preferably between 8 to 24 hours.

(g) Geopolymer substrate curing environment: The curing of the geopolymer composition according to this invention may be carried out in presence of air, moisture, steam, carbon dioxide, flue gas, inert gases, water, organic solvents, or other gases or liquids. Most preferably the curing is carried out in the presence of moisture, water, or steam.

(h) Geopolymer substrate post-curing hydrothermal treatment medium: The cured geopolymer substrates can be partly converted to zeolite by hydrothermal treatment in water or other hydrothermal treatment media including alkali or alkaline earth metal solution, zeolite synthesis precursor solution, and solvents. Additionally, the post-curing treatment can be conducted by simply heating in the presence of the moisture released from the geopolymer mixture or externally generated steam.

(i) Geopolymer substrate post-curing hydrothermal treatment temperature and time: The geopolymer substrate post-curing hydrothermal treatment is carried out by heating in a hydrothermal treatment medium at a temperature necessary to further improve its strength or convert part of the geopolymer into zeolite. Depending on the type of geopolymer composition and desired zeolite type, the post-curing hydrothermal treatment is generally performed at a temperature below 250° C., advantageously below 200° C., preferably below 150° C. and within the range of 40 to 150° C., and most preferably within the range 60 to 120° C. The zeolite hydrothermal synthesis time is generally between 1 and 168 h, preferably between 1 and 72 hours, more preferably between 2 to 48 hours, even more preferably between 4 to 24 hours.

(j) Zeolite seeding material: Zeolites typically have Si and Al joined by an oxygen bridge, and an overall negative charge, which requires positively charged counter ions, such as Na+, K+, and Ca2+. The zeolite may be a hydrophilic zeolite or hydrophobic zeolite. Representative examples are zeolites of the structure types AFI, AEL, BEA, CHA, EUO, FAU, FER, KFI, LTA, LTL, MAZ, MOR, MFI, MEL, MTW, OFF and TON. Examples of the crystal system include zeolites A, X, Y, T, P, β, and ZSM-5, silicalite, and mordenite. Zeolite seed particles can be synthesized utilizing a chemical process, for example, a hydrothermal process. Zeolite seed particles can also be prepared by grinding or ball-milling commercially available synthesized or natural zeolite powders having large particle sizes into smaller particles sizes.

(k) Zeolite seed application process: The zeolite seed application can be performed by a variety of coating processes, including rubbing, brushing, dip-coating, vacuum application, flow-coating, spray coating, slip casting, immersion or others known to those skilled in the art. The zeolite seeds can be applied as a powder directly or dispersed in a coating fluid. The coating comprising zeolite seeds can be applied from a coating composition that further comprises a dispersant, a binder, an anti-cracking agent, an anti-foam agent or combinations thereof. Additionally zeolite seeding can be done by mixing zeolite seeds into the geopolymer mixture.

(l) Zeolite membrane hydrothermal synthesis precursor solution: The zeolite precursor solution used in the zeolite membrane hydrothermal synthesis includes an alumina source and a silica source, and may also include an alkali metal source and/or an alkaline earth metal source depending on necessity. Examples of the alumina source include an aluminum salt, such as aluminum hydroxide, sodium aluminate, aluminum sulfate, aluminum nitrate and aluminum chloride, alumina powder and colloidal alumina. Examples of the silica source include an alkali metal silicate, such as sodium silicate, water glass and potassium silicate, silica powder, silicic acid, colloidal silica and a silicon alkoxide. Examples of the alkali metal source and the alkaline earth metal source include sodium oxide, sodium chloride, potassium chloride, calcium chloride and magnesium chloride. The composition of the synthesis precursor solution may be appropriately determined depending on the composition of the target zeolite.

(m) Zeolite membrane hydrothermal synthesis temperature and time: The zeolite membrane hydrothermal synthesis is advantageously carried out by contacting the substrate in the zeolite synthesis precursor solution and heating at a temperature necessary to effect zeolite crystallization, often in an autoclave under autogenous pressure. Depending on the type of zeolite to be synthesized, the zeolite hydrothermal synthesis is generally performed at a temperature below 400° C., advantageously below 250° C., preferably below 150° C. and within the range of 60 to 150° C., and most preferably within the range 80 to 120° C. The zeolite hydrothermal synthesis time is generally between 1 and 168 h, preferably between 1 and 72 hours, more preferably between 2 to 48 hours, even more preferably between 4 to 24 hours.

The following are optional:

(n) Organic binder: Organic binders can be optionally added as part of the geopolymer composition to adjust. All organic binders conventionally used in conventional ceramic process can be used. Examples of organic binders include ethyl cellulose group, methyl cellulose group; guar gum, starch, cellulose gums, acrylic polymers, polyethylene glycol, polyvinyl alcohol, or a mixture thereof.

(o) Fillers: The geopolymer composition according to the invention may optionally include one or more filler materials to provide ductility, resiliency, roughness, or other properties to the geopolymer. Any fillers known in the art, or combinations thereof, may be used. Exemplary fillers include, but are not limited to zeolites, ceramic powder, glass powder, fibers, sand, polymer materials, ground shell powder, wood, carbon black, graphite, mica, even nanosized materials.

(p) Forming surface for geopolymer substrate fabrication:
The geopolymer substrates can be fabricated on a forming surface. The forming surface may have various configurations. For example, the surface may be flat, curved, a hollow cylinder or honeycomb-shaped. The supporting substrates can be porous or non-porous in microstructure. The porous supporting substrates can be removed after geopolymer substrate fabrication and curing or remain as an integral part of the overall supported membranes. The supporting substrate material can be selected from ceramics, metals, or organic polymers.

(q) Geopolymer substrate surface polishing:
The geopolymer substrates can be optionally treated by polishing one or more of its surfaces. Polishing can be performed, for example, by rubbing the surfaces with a polishing material (e.g., a polishing paper). The properties of the polishing material can vary, depending on the application. In one exemplary implementation, the surfaces of the substrate can be polished with a silicon carbide polishing paper in order to reduce the roughness of those surfaces.

(r) Geopolymer substrate surface masking:
In the present invention, it is not necessary to mask the geopolymer substrates prior to zeolite membrane hydrothermal synthesis to prevent zeolite synthesis precursor solution from contacting the unseeded side of the substrates and blocking substrate pores. However, the geopolymer substrates can be optionally masked as desired to prevent undesired reactions or contaminations. A barrier layer can be applied to the outer surface of the geopolymer substrates, for example by spraying, wrapping, coating or combinations thereof. Any material capable of withstanding the zeolite membrane hydrothermal synthesis process can be used as the barrier layer such as a wrap or a coating comprising a material, for example, a metal, a polymer coating, a polymer wrap, Teflon, a plastic wrap, saran wrap, shrink wrap tubing, epoxy, a glass, a ceramic, a rubber, a latex and the like, and combinations thereof.

(s) Zeolite structure directing agent: Zeolite structure directing agents can be advantageously introduced into the zeolite synthesis precursor solution to aid the crystallization of desired zeolites. The structure directing agent may be, for example, the hydroxide or salt of tetramethylammonium (TMA), tetraethylammonium (TEA), triethylmethylammonium (TEMA), tetrapropylammonium (TPA), tetrabutylammonium (TBA), etc.

(t) Zeolite membrane hydrothermal synthesis repetition: The zeolite membrane hydrothermal synthesis process can be carried out two or more times as needed to reduce the defects in the zeolite membranes.

(u) Zeolite ion exchange: The zeolite membranes can be optionally ion-exchanged to obtain desired membrane properties and functionalities. Ion exchange of zeolites is carried out by contacting the zeolites using batch-wise or continuous processes with aqueous solutions of salts of the cations to be introduced.

(v) Zeolite membrane calcination: For certain types of zeolites, a final calcination step is necessary to burn off the organic molecules including structure directing agents in the pore structure, thus providing an internal pore structure available for adsorption or ion exchange. The calcination temperature is generally in the range of about 150 to 600° C.

Comparative Example A

Geopolymer composition: Argical-M1000 metakaolin, sodium silicate, and sodium hydroxide; Geopolymer curing: 60° C. for 24 h; Geopolymer hydrothermal treatment: 90° C. in water for 24 h; Zeolite seeding: no; Zeolite membrane hydrothermal synthesis: no.

In this example, a geopolymer composition is prepared by mixing Argical M1000 metakaolin with a pre-mixed sodium silicate and sodium hydroxide activator solution. The geopolymer mixture comprises 45 wt % of metakaolin (Argical M1000, Imerys, Roswell, Ga.), 29 wt % of sodium silicate solution (Grade 20 Clear, Occidental Chemical Corporation, Dallas, Tex.), and 26 wt % of sodium hydroxide solution (50% caustic soda diaphragm, Occidental Chemical Corporation, Dallas, Tex.). The geopolymer mixture is mixed using a high shear mixer until a uniform mixture is obtained. The geopolymer mixture is cast into a disc shaped mold of 25 mm in diameter and 6 mm in thickness. The disc mold is sealed and cured at 60° C. for 24 h before demolding. X-ray diffraction (XRD) analysis conducted using a Rigaku Ultima III powder diffractometer indicates that the cured geopolymer is amorphous geopolymer with some peaks from quartz which is an impurity in the metakaolin raw material.

The demolded geopolymer disc is placed into de-ionized water to carry out hydrothermal treatment at 90° C. for 24 h. XRD analysis of the hydrothermally treated geopolymer shows that faujasite zeolite emerges as part of the geopolymer microstructure after the hydrothermal treatment. The hydrothermally treated geopolymer disc is washed with de-ionized water and dried for ethanol dehydration evaluation. No zeolite seeding or zeolite hydrothermal synthesis using zeolite precursor solutions is performed to fabricate zeolite membranes on the geopolymer disc produced.

For membrane dehydration performance evaluation, a mixture of 90% ethanol and 10% water is used as the feed. The permeate side of the membrane is connected to a liquid nitrogen cold trap to collect water and the pressure is maintained <300 Pa using a vacuum pump. Dehydration evaluation of the membranes is conducted at 50° C. The compositions of the feed mixture and permeate is analyzed using a Shimadzu GC-2014 Gas Chromatography. Permeation flux is defined as the total amount of permeated liquid in kg per hour (h) per unit area in $m^2$ of the membrane that is exposed to the feed mixture. Separation factor is defined as the weight percentage of water in the permeate divided by the weight percentage of water in the feed divided by the weight percentage of ethanol in the permeate multiplied by the weight percentage of ethanol in the feed. The geopolymer disc fabricated in this example has a separation factor of 5 and permeation flux of 4.78 kg/$m^2$ h in the separation of 90% ethanol and 10% water at 50° C.

Comparative Example B

Geopolymer composition: PowerPozz metakaolin, sodium silicate, and sodium hydroxide; Geopolymer curing: 60° C. for 24 h; Geopolymer hydrothermal treatment: 90° C. in water for 24 h; Zeolite seeding: no; Zeolite membrane hydrothermal synthesis: no.

In this example, a geopolymer composition is prepared by mixing PowerPozz metakaolin with a pre-mixed sodium silicate and sodium hydroxide activator solution. The geopolymer mixture comprises 42 wt % of metakaolin (PowerPozz Standard Grade, Advanced Cement Technologies, Blaine, Wash.), 46 wt % of sodium silicate solution (Grade 20 Clear, Occidental Chemical Corporation, Dallas, Tex.), and 12 wt % of sodium hydroxide solution (50% caustic soda diaphragm, Occidental Chemical Corporation, Dallas, Tex.). The geopolymer mixture and discs are prepared the same way as that in Comparative Example A. The hydrothermally treated geopolymer discs are washed with de-ionized water and dried for ethanol dehydration evaluation. No zeolite seeding or zeolite hydrothermal synthesis using zeolite precursor solutions is performed to fabricate zeolite membranes on the geopolymer discs produced.

The membrane dehydration performance evaluation is carried out the same way as that in Comparative Example A. The geopolymer disc fabricated in this example has a separation factor of 2 and permeation flux of 3.15 kg/$m^2$ h in the separation of 90% ethanol and 10% water at 50° C.

Example 1

Geopolymer composition: the same as Comparative Example A; Geopolymer curing: ambient temperature for 24 h followed by 60° C. for 1 h; Geopolymer hydrothermal treatment: 90° C. in water for 24 h; zeolite seeding: seeding after geopolymer hydrothermal treatment (once); Substrate masking prior to zeolite hydrothermal synthesis: yes; Zeolite synthesis precursor solution composition: $2SiO_2:Al_2O_3:$ $2.1Na_2O:140H_2O$; Zeolite membrane hydrothermal synthesis: 90° C. in zeolite synthesis solution for 8 h.

In this example, the geopolymer composition is prepared the same way as that in Comparative Example A. After mixing, the geopolymer mixture is cast into a disc shaped mold of 25 mm in diameter and 3 mm in thickness. The disc mold is sealed and cured at ambient temperature for 24 h and then at 60° C. for 1 h before demolding. XRD analysis indicates that the substrate is amorphous geopolymer with some quartz impurity peaks. The demolded geopolymer disc is placed into de-ionized water to carry out hydrothermal treatment at 90° C. for 24 h. XRD analysis shows that faujasite zeolite emerges as part of the geopolymer substrate. The hydrothermally treated geopolymer disc is washed with de-ionized water before using as the substrate for zeolite membrane fabrication.

In this example, a secondary growth method is used to fabricate zeolite membrane on the geopolymer substrate by seeding with zeolite powder followed with hydrothermal synthesis in a zeolite synthesis precursor solution. The geopolymer substrate is covered on one side using Teflon tape, leaving the other side of the disc open for zeolite seeding and subsequent zeolite membrane hydrothermal synthesis. Zeolite A powder (<10 microns powder, Sigma-Aldrich, St. Louis, Mo.) is evenly rubbed onto the open side of the geopolymer substrate.

The seeded geopolymer substrate is immersed into a zeolite synthesis precursor solution to carry out zeolite membrane hydrothermal synthesis on the geopolymer substrate. The zeolite synthesis solution is prepared by mixing sodium silicate solution (Grade 20 Clear, Occidental Chemical Corporation, Dallas, Tex.), sodium aluminate solution (USALCO 38, USALCO, LLC, Baltimore, Md.), sodium hydroxide solution (50% caustic soda diaphragm, Occidental Chemical Corporation, Dallas, Tex.), and de-ionized water to form a sol having a molar composition of $2SiO_2:$ $Al_2O_3:2.1Na_2O:140H_2O$. The zeolite hydrothermal synthesis is conducted at 90° C. for 8 h. XRD analysis of the zeolite membrane supported on the geopolymer substrate indicates that zeolite A membrane is successfully formed on the substrate. After the hydrothermal synthesis, the zeolite membrane is rinsed with de-ionized water and dried for ethanol dehydration evaluation.

The membrane dehydration performance evaluation is carried out the same way as that in Comparative Example A. The seeded side of the membrane is in contact with the feed and the unseeded side is connected to the cold trap. The zeolite membrane fabricated in this example has a separation factor of >10000 and permeation flux of 1.33 kg/$m^2$ h in the separation of 90% ethanol and 10% water at 50° C. The separation selectivity of the geopolymer supported zeolite membrane fabricated in this example is much higher than that of the geopolymer substrate in Comparative Example A and comparable to those of the best performing conventional supported zeolite membranes (>5000-10000) in prior art.

The permeation flux is also higher than most of the conventional supported zeolite membranes reported at the same temperature in prior art.

Example 2

Membrane fabrication is the same as Example 1 except the following: Geopolymer curing: 60° C. for 24 h; Zeolite membrane hydrothermal synthesis: 90° C. in zeolite synthesis solution for 6 h.

In this example, the geopolymer substrate is fabricated the same way as that in Example 1 except that the geopolymer curing is conducted at 60° C. for 24 h. XRD analysis indicates that the substrate is amorphous geopolymer with some quartz impurity peaks after curing and faujasite zeolite emerges after geopolymer hydrothermal treatment in water at 90° C. for 24 h. The zeolite membrane fabrication on the geopolymer substrate in this example is the same as that in Example 1 except that the zeolite hydrothermal synthesis is conducted at 90° C. for 6 h. XRD analysis of the zeolite membrane supported on the geopolymer substrate indicates that zeolite A is successfully formed on the substrate after zeolite hydrothermal synthesis. Scanning electron microscopy (SEM) characterization of the cross-section of the supported zeolite membrane confirms the formation of a thin layer of zeolite membrane of a few microns in thickness on the geopolymer substrate. After the hydrothermal synthesis, the zeolite membrane is rinsed with de-ionized water and dried for ethanol dehydration evaluation.

The membrane dehydration performance evaluation is carried out the same way as that in Example 1. The zeolite membrane fabricated in this example has a separation factor of >10000 and permeation flux of 2.07 kg/m$^2$ h in the separation of 90% ethanol and 10% water at 50° C. When the ethanol dehydration is conducted at 75° C., the membrane demonstrates a separation factor of >10000 and permeation flux of 3.67 kg/m$^2$ h. The separation selectivity of the geopolymer supported zeolite membrane fabricated in this example is significantly higher than that of the geopolymer substrate in Comparative Example A and comparable to those of the best performing conventional supported zeolite membranes (>5000-10000) in prior art. The permeation flux is also higher than most of the conventional supported zeolite membranes reported at the same temperature in prior art.

Example 3

Membrane fabrication is the same as Example 2 except the following: Substrate masking prior to zeolite hydrothermal synthesis: no; Zeolite membrane hydrothermal synthesis: 90° C. in zeolite synthesis solution for 8 h.

In this example, the geopolymer substrate is fabricated the same way as that in Example 2. The zeolite membrane fabrication on the geopolymer substrate in this example is the same as that in Example 2 except that the geopolymer substrate is used directly without any surface masking and zeolite hydrothermal synthesis is conducted at 90° C. for 8 h.

The membrane dehydration performance evaluation is carried out the same way as that in Example 1. The zeolite membrane fabricated in this example has a separation factor of >10000 and permeation flux of 2.2 kg/m$^2$ h in the separation of 90% ethanol and 10% water at 50° C. When the ethanol dehydration is conducted at 75° C., the membrane demonstrates a separation factor of >10000 and permeation flux of 4.07 kg/m$^2$ h. The separation selectivity of the geopolymer supported zeolite membrane fabricated in this example is significantly higher than that of the geopolymer substrate in Comparative Example A and comparable to those of the best performing conventional supported zeolite membranes (>5000-10000) in prior art. The permeation flux is also higher than most of the conventional supported zeolite membranes reported at the same temperature in prior art.

Example 4

Membrane fabrication is the same as Example 3 except the following: Zeolite seeding: seeding before geopolymer hydrothermal treatment (once); Substrate masking prior to zeolite hydrothermal synthesis: yes.

In this example, the geopolymer substrate is fabricated the same way as that in Example 3. The zeolite membrane fabrication on the geopolymer substrate in this example is the same as that in Example 3 except that the geopolymer substrate is masked on one side with Teflon tape and seeded with zeolite A powder on the other side after geopolymer curing at 60° C. for 24 h. The seeded geopolymer substrate is then subjected to hydrothermal treatment at 90° C. in water for 24 h.

The membrane dehydration performance evaluation is carried out the same way as that in Example 1. The zeolite membrane fabricated in this example has a separation factor of 2096 and permeation flux of 1.72 kg/m$^2$ h in the separation of 90% ethanol and 10% water at 50° C. The separation selectivity of the geopolymer supported zeolite membrane fabricated in this example is significantly improved over that of the geopolymer substrate in Comparative Example A. The permeation flux is also higher than most of the conventional supported zeolite membranes reported at the same temperature in prior art.

Example 5

Membrane fabrication is the same as Example 4 except the following: Zeolite seeding: seeding both before and after hydrothermal treatment (twice); Substrate masking prior to zeolite hydrothermal synthesis: no.

In this example, the geopolymer substrate is fabricated the same way as that in Example 4. The zeolite membrane fabrication on the geopolymer substrate in this example is the same as that in Example 4 except that the geopolymer substrate is used directly without surface masking, and is seeded both before and after hydrothermal treatment. The cured geopolymer substrate is seeded with zeolite A powder and subjected to hydrothermal treatment at 90° C. in water for 24 h. The hydrothermally treated geopolymer substrate is then seeded again with zeolite A powder and subjected to zeolite membrane hydrothermal synthesis in zeolite synthesis solution for 8 h to fabricate zeolite membrane.

The membrane dehydration performance evaluation is carried out the same way as that in Example 1. The zeolite membrane fabricated in this example has a separation factor of >10000 and permeation flux of 1.99 kg/m$^2$ h in the separation of 90% ethanol and 10% water at 50° C. T The separation selectivity of the geopolymer supported zeolite membrane fabricated in this example is significantly higher than that of the geopolymer substrate in Comparative Example A and comparable to those of the best performing conventional supported zeolite membranes (>5000-10000) in prior art. The permeation flux is also higher than most of the conventional supported zeolite membranes reported at the same temperature in prior art.

Example 6

Membrane fabrication is the same as Example 5 except the following: Zeolite membrane hydrothermal synthesis: 90° C. in zeolite synthesis solution for 24 h In this example, the geopolymer substrate is fabricated the same way as that in Example 5. The zeolite membrane fabrication on the geopolymer substrate in this example is the same as that in Example 5 except that the seeded geopolymer substrate is subjected to zeolite membrane hydrothermal synthesis in zeolite synthesis solution for 24 h to fabricate zeolite membrane.

The membrane dehydration performance evaluation is carried out the same way as that in Example 1. The zeolite membrane fabricated in this example has a separation factor of >10000 and permeation flux of 2.05 kg/m$^2$ h in the separation of 90% ethanol and 10% water at 50° C. T The separation selectivity of the geopolymer supported zeolite membrane fabricated in this example is significantly higher than that of the geopolymer substrate in Comparative Example A and comparable to those of the best performing conventional supported zeolite membranes (>5000-10000) in prior art. The permeation flux is also higher than most of the conventional supported zeolite membranes reported at the same temperature in prior art.

Example 7

Membrane fabrication is the same as Example 2 except the following: Zeolite seeding: seeding before geopolymer molding and after hydrothermal treatment (twice); Zeolite membrane hydrothermal synthesis: 90° C. in zeolite synthesis solution for 8 h.

In this example, the geopolymer substrate is fabricated the same way as that in Example 2 except that a thin layer of zeolite A powder is deposited on the bottom plate of the mold before geopolymer molding. The zeolite membrane fabrication on the geopolymer substrate in this example is the same as that in Example 2 except that the seeded geopolymer substrate is subjected to zeolite membrane hydrothermal synthesis in zeolite synthesis solution for 8 h to fabricate zeolite membrane.

The membrane dehydration performance evaluation is carried out the same way as that in Example 1. The zeolite membrane fabricated in this example has a separation factor of 7896 and permeation flux of 2.46 kg/m$^2$ h in the separation of 90% ethanol and 10% water at 50° C. The separation selectivity of the geopolymer supported zeolite membrane fabricated in this example is significantly higher than that of the geopolymer substrate in Comparative Example A and comparable to those of the best performing conventional supported zeolite membranes (>5000-10000) in prior art. The permeation flux is also higher than most of the conventional supported zeolite membranes reported at the same temperature in prior art.

Example 8

Membrane fabrication is the same as Example 7 except the following: Geopolymer curing: 60° C. for 48 h.

In this example, the geopolymer substrate is fabricated the same way as that in Example 7 except that the geopolymer substrate is cured at 60° C. for 48 h.

The membrane dehydration performance evaluation is carried out the same way as that in Example 1. The zeolite membrane fabricated in this example has a separation factor of 5622 and permeation flux of 1.82 kg/m$^2$ h in the separation of 90% ethanol and 10% water at 50° C. T The separation selectivity of the geopolymer supported zeolite membrane fabricated in this example is significantly higher than that of the geopolymer substrate in Comparative Example A and comparable to those of the best performing conventional supported zeolite membranes (>5000-10000) in prior art. The permeation flux is also higher than most of the conventional supported zeolite membranes reported at the same temperature in prior art.

Example 9

Membrane fabrication is the same as Example 3 except the following: Geopolymer composition: 45 wt % Argical metakaolin, 40 wt % sodium silicate, and 15 wt % sodium hydroxide.

In this example, the geopolymer substrate is fabricated the same way as that in Example 3 except that the geopolymer mixture comprises 45 wt % of metakaolin (Argical M1000, Imerys, Roswell, Ga.), 40 wt % of sodium silicate solution (Grade 20 Clear, Occidental Chemical Corporation, Dallas, Tex.), and 15 wt % of sodium hydroxide solution (50% caustic soda diaphragm, Occidental Chemical Corporation, Dallas, Tex.).

The membrane dehydration performance evaluation is carried out the same way as that in Example 1. The zeolite membrane fabricated in this example has a separation factor of >10000 and permeation flux of 0.6 kg/m$^2$ h in the separation of 90% ethanol and 10% water at 50° C. T The separation selectivity of the geopolymer supported zeolite membrane fabricated in this example is significantly higher than that of the geopolymer substrate in Comparative Example A and comparable to those of the best performing conventional supported zeolite membranes (>5000-10000) in prior art. The permeation flux is comparable to most of the conventional supported zeolite membranes reported at the same temperature in prior art.

Example 10

Membrane fabrication is the same as Example 2 except the following: Geopolymer composition: 46 wt % Argical metakaolin, 28 wt % sodium silicate, and 26 wt % sodium hydroxide; Geopolymer hydrothermal treatment: no; Zeolite membrane hydrothermal synthesis: 90° C. in zeolite synthesis solution for 8 h; Zeolite membrane hydrothermal synthesis repetition: one time.

In this example, the geopolymer substrate is fabricated the same way as that in Example 2 except that the geopolymer mixture has an increased metakaolin loading, the cured geopolymer substrate does not undergo post-curing hydrothermal treatment in water at 90° C., and the zeolite membrane hydrothermal synthesis is repeated one time. The geopolymer mixture comprises 46 wt % of metakaolin (Argical M1000, Imerys, Roswell, Ga.), 28 wt % of sodium silicate solution (Grade 20 Clear, Occidental Chemical Corporation, Dallas, Tex.), and 26 wt % of sodium hydroxide solution (50% caustic soda diaphragm, Occidental Chemical Corporation, Dallas, Tex.). The cured geopolymer substrate is used directly as the membrane support and undergoes seeding and hydrothermal synthesis in zeolite synthesis precursor solution to fabricate zeolite membrane. After the zeolite membrane hydrothermal synthesis, the zeolite membrane is washed with de-ionized water and immersed into a new batch of zeolite synthesis precursor solution to perform the zeolite hydrothermal synthesis one more time.

The membrane dehydration performance evaluation is carried out the same way as that in Example 1. The zeolite membrane fabricated in this example has a separation factor of 1576 and permeation flux of 1.43 kg/m$^2$ h in the separation of 90% ethanol and 10% water at 50° C. T.

Example 11

Membrane fabrication is the same as Example 5 except the following: Zeolite synthesis precursor solution composition: $1.8SiO_2:Al_2O_3:3.6Na_2O:270H_2O$.

In this example, the geopolymer substrate is fabricated the same way as in Example 5 except that the zeolite synthesis solution is prepared by mixing sodium silicate solution (Grade 20 Clear, Occidental Chemical Corporation, Dallas, Tex.), sodium aluminate solution (USALCO 38, USALCO, LLC, Baltimore, Md.), sodium hydroxide solution (50% caustic soda diaphragm, Occidental Chemical Corporation, Dallas, Tex.), and de-ionized water to form a sol having a molar composition of $1.8SiO_2:Al_2O_3:3.6Na_2O:270H_2O$.

The membrane dehydration performance evaluation is carried out the same way as that in Example 1. The zeolite membrane fabricated in this example has a separation factor of >10000 and permeation flux of 1.2 kg/m$^2$ h in the separation of 90% ethanol and 10% water at 50° C. T The separation selectivity of the geopolymer supported zeolite membrane fabricated in this example is significantly higher than that of the geopolymer substrate in Comparative Example A and comparable to those of the best performing conventional supported zeolite membranes (>5000-10000) in prior art. The permeation flux is comparable to most of the conventional supported zeolite membranes reported at the same temperature in prior art.

Example 12

Geopolymer composition: the same as Comparative Example B: Geopolymer curing: 60° C. for 24 h; Geopolymer hydrothermal treatment: 90° C. in water for 24 h; Zeolite seeding: seeding both before and after hydrothermal treatment (twice); Substrate masking prior to zeolite hydrothermal synthesis: yes; Zeolite synthesis precursor solution composition: $2SiO_2:Al_2O_3:2.1Na_2O:140H_2O$; Zeolite membrane hydrothermal synthesis: 90° C. in zeolite synthesis solution for 8 h; Zeolite membrane hydrothermal synthesis repetition: one time.

In this example, the geopolymer composition is prepared the same way as that in Comparative Example B. After mixing, the geopolymer mixture is cast into a disc shaped mold of 25 mm in diameter and 3 mm in thickness. The disc mold is sealed and cured at 60° C. for 24 h before demolding. After curing, the geopolymer substrate is masked on one side with Teflon tape and seeded with zeolite A powder on the other side. The seeded geopolymer substrate is subjected to hydrothermal treatment at 90° C. in water for 24 h. The hydrothermally treated geopolymer substrate is then seeded again with zeolite A powder and subjected to zeolite membrane hydrothermal synthesis in a zeolite synthesis solution with a composition of $2SiO_2:Al_2O_3:2.1Na_2O:140H_2O$ at 90° C. for 8 h to fabricate zeolite membrane. After the zeolite membrane hydrothermal synthesis, the zeolite membrane is washed with de-ionized water and immersed into another batch of zeolite synthesis precursor solution to perform the zeolite hydrothermal synthesis one more time.

The membrane dehydration performance evaluation is carried out the same way as that in Example 1. The zeolite membrane fabricated in this example has a separation factor of >10000 and permeation flux of 0.96 kg/m$^2$ h in the separation of 90% ethanol and 10% water at 50° C. The separation selectivity of the geopolymer supported zeolite membrane fabricated in this example is much higher than that of the geopolymer substrate in Comparative Example B and comparable to those of the best performing conventional supported zeolite membranes (>5000-10000) in prior art. The permeation flux is also higher than most of the conventional supported zeolite membranes reported at the same temperature in prior art.

CONCLUSION

While the instant invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains.

What is claimed is:

1. An asymmetric membrane, comprising: (1) a geopolymer layer as a substrate; (2) ex-situ produced zeolite seed crystals layered on the geopolymer substrate; and (3) a layer of zeolite surface grown on the zeolite see crystal layer.

2. The asymmetric membrane of claim 1, wherein the zeolite seed crystals have crystallized with the zeolite surface layer.

3. The asymmetric membrane of claim 1, wherein the geopolymer substrate has the zeolite seed crystals added to the geopolymer composition prior to forming the geopolymer substrate.

4. The asymmetric membrane of claim 1, wherein the zeolite is selected from A, X, Y, T, P, β, ZSM-5, silicalite, or mordenite type zeolites.

5. The asymmetric membrane of claim 1, wherein the zeolite is an A type zeolite.

6. A process for making an asymmetric membrane of claim 1, comprising:
   (a) preparing a geopolymer composition wherein an aluminosilicate source and an alkali activator selected from an alkali metal silicate; an alkaline earth metal silicate; an alkali metal hydroxide; or an alkaline earth metal hydroxide;
   (b) forming a geopolymer substrate from the geopolymer composition of (a) by processes known in the art;
   (c) depositing zeolite seed crystals on the geopolymer substrate of (b) to form a seeded geopolymer substrate;
   (d) immersing the seeded geopolymer substrate of (c) into a liquid composition comprising silica and alumina source materials; and
   (e) subjecting the geopolymer substrate of (d) to hydrothermal synthesis to form a surface layer comprising a zeolite on the geopolymer substrate layer.

7. The process of claim 6 (a), wherein the aluminosilicate source is selected from metakaolin, calcined clays, fly ash, or combinations thereof.

8. The process of claim 6 (a), wherein the geopolymer composition comprises an aluminosilicate source comprising metakaolin, an alkali activator comprising sodium silicate and sodium hydroxide, and water.

9. The process of claim 6 (a), wherein the molar ratio of $SiO_2$ to $Al_2O_3$ of the silica and alumina source material is from about 2 to about 4 and the molar ratio of $M_2O$ to $Al_2O_3$ of the silica and alumina source material is from about 0.5 to about 2, wherein M is an alkali cation.

10. The process of claim 6 (a), wherein the molar ratio of $SiO_2$ to $Al_2O_3$ of the silica and alumina source material is from about 2.5 to about 3.5 and a molar ratio of $M_2O$ to $Al_2O_3$ is from about 0.8 to about 1.6, wherein M is an alkali cation.

11. The process of claim 6 (e), wherein the zeolite hydrothermal synthesis comprises heating the geopolymer substrate to a temperature between about 30 to about 200° C. for a period of time between about 1 to about 168 hours to produce the asymmetric membrane.

12. A process for making an asymmetric membrane of claim 1, comprising:
  (a) preparing a geopolymer composition comprising an aluminosilicate source and an alkali activator selected from an alkali metal silicate; an alkaline earth metal silicate; an alkali metal hydroxide; or an alkaline earth metal hydroxide;
  (b) forming a geopolymer substrate from the geopolymer composition of (a) under conditions of hydrothermal treatment in water or in an alkali solution that produces zeolite crystals in the geopolymer substrate;
  (c) depositing zeolite seed crystals on the geopolymer substrate to form a seeded geopolymer substrate;
  (d) immersing the seeded geopolymer substrate of (c) into a liquid composition comprising aluminosilicate and silica source materials; and
  (e) subjecting the geopolymer substrate of (d) to hydrothermal synthesis to form a layer comprising a zeolite on the geopolymer substrate layer.

13. The process of claim 12 (a), wherein the aluminosilicate source is selected from metakaolin, calcined clays, fly ash, or combinations thereof.

14. The process of claim 12 (a), wherein the geopolymer composition comprises an aluminosilicate source comprising metakaolin, an alkali activator comprising sodium silicate and sodium hydroxide, and water.

15. The process of claim 12 (a), wherein the molar ratio of $SiO_2$ to $Al_2O_3$ of the silica and alumina source material is from about 2 to about 4 and a molar ratio of $M_2O$ to $Al_2O_3$ of the silica and alumina source material is from about 0.5 to about 2, wherein M is an alkali cation.

16. The process of claim 12 (a), wherein the molar ratio of $SiO_2$ to $Al_2O_3$ of the silica and alumina source material is from about 2.5 to about 3.5 and a molar ratio of $M_2O$ to $Al_2O_3$ from about 0.8 to about 1.6, wherein M is an alkali cation.

17. The process of claim 12 (c), wherein the zeolite hydrothermal synthesis comprises heating the geopolymer substrate to a temperature between about 30 to about 200° C. for a period of time between about 1 to about 168 hours to produce the asymmetric membrane.

18. The asymmetric membrane of claim 1, wherein the geopolymer substrate is derived from a geopolymer composition having an aluminosilicate source and an alkali activator.

19. The process of claim 6 (c), wherein the zeolite seed crystals are applied to the geopolymer substrate by a coating process selected from rubbing, brushing, dip-coating, vacuum application, flow-coating, spray coating, slip casting, immersion or other known processes.

20. The process of claim 6 (c), wherein the zeolite seed crystals can be applied as a powder directly to the geopolymer substrate or by dispersing the seed crystals in a coating fluid.

21. A cross-flow membrane separation method for increasing the concentration of chemicals by dehydration using the asymmetric merribrane of claim 1.

22. The method of claim 21, wherein the chemicals are found in organic solvents, oil, wines and juices, industrial gases, petrochemicals, and environmental remediation.

23. The method of claim 21 for increasing the concentration of ethanol from a feed mixture having water and ethanol, comprising: (a) cross-flowing the feed mixture across the asymmetric membrane of claim 1, wherein the pressure of the feed mixture on the zeolite surface layer is greater than the pressure of the geopolymer layer across the asymmetric membrane, and (b) producing a permeate having an ethanol concentration less than the ethanol concentration of the feed mixture and a retentate having an ethanol concentration greater than the ethanol concentration of the feed mixture.

24. A cross-membrane separation method for removing water from an aqueous system or gaseous system by dehydration using the asymmetric membrane of claim 1.

25. The method of claim 23, wherein the aqueous or gaseous system is from wastewater treatment, organic solvents, oil, or purification of either water or chemicals.

* * * * *